US008676328B2

(12) United States Patent
Sauter-Starace et al.

(10) Patent No.: US 8,676,328 B2
(45) Date of Patent: Mar. 18, 2014

(54) TRANSCRANIAL SECURING DEVICE FOR DEEP BRAIN STIMULATION LEADS

(75) Inventors: Fabien Sauter-Starace, Seyssinet-Pariset (FR); Alim-Louis Benabid, Meylan (FR); Raymond Charles, Saint Jean de Morains (FR)

(73) Assignee: Commissariat a l'Energie Atomique, Paris (FR)

( * ) Notice: Subject to any disclaimer, the term of this patent is extended or adjusted under 35 U.S.C. 154(b) by 568 days.

(21) Appl. No.: 12/603,062

(22) Filed: Oct. 21, 2009

(65) Prior Publication Data
US 2010/0161018 A1 Jun. 24, 2010

(30) Foreign Application Priority Data
Oct. 23, 2008 (FR) ...................................... 08 05873

(51) Int. Cl.
*A61N 1/00* (2006.01)
(52) U.S. Cl.
USPC ............................................................ 607/45
(58) Field of Classification Search
USPC .................................. 607/45, 116, 129, 130
See application file for complete search history.

(56) References Cited

U.S. PATENT DOCUMENTS

| 6,134,477 | A | * | 10/2000 | Knuteson ....................... 607/115 |
| 6,321,104 | B1 | | 11/2001 | Gielen et al. |
| 6,356,792 | B1 | * | 3/2002 | Errico et al. .................. 607/116 |
| 7,004,948 | B1 | | 2/2006 | Pianca et al. |
| 7,302,298 | B2 | | 11/2007 | Lowry et al. |
| 8,043,304 | B2 | * | 10/2011 | Barker .......................... 606/129 |
| 2004/0034367 | A1 | | 2/2004 | Malinowski |
| 2005/0182420 | A1 | | 8/2005 | Schulte et al. |

* cited by examiner

*Primary Examiner* — Christopher D Koharski
*Assistant Examiner* — Nadia Ahmad
(74) *Attorney, Agent, or Firm* — Morgan, Lewis & Bockius LLP

(57) ABSTRACT

A transcranial securing device for deep brain stimulation leads comprising: a principal part for securing inside an opening formed in the cranium of a patient; and at least one first securing part housed inside said principal part; said or each securing part comprises at least one axial bore adapted to allow the passage of one or more deep brain stimulation leads; said or at least one securing part is arranged so as to be capable of passing from a first position in which the lead or leads can slide axially in the respective bores, to a second position in which it grips the lead or leads in the respective bore or bores, preventing said sliding.

8 Claims, 3 Drawing Sheets

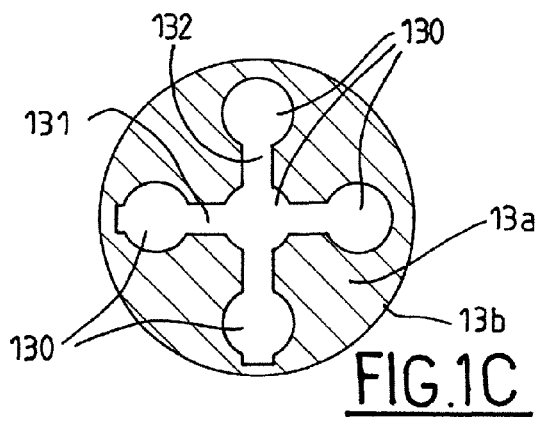
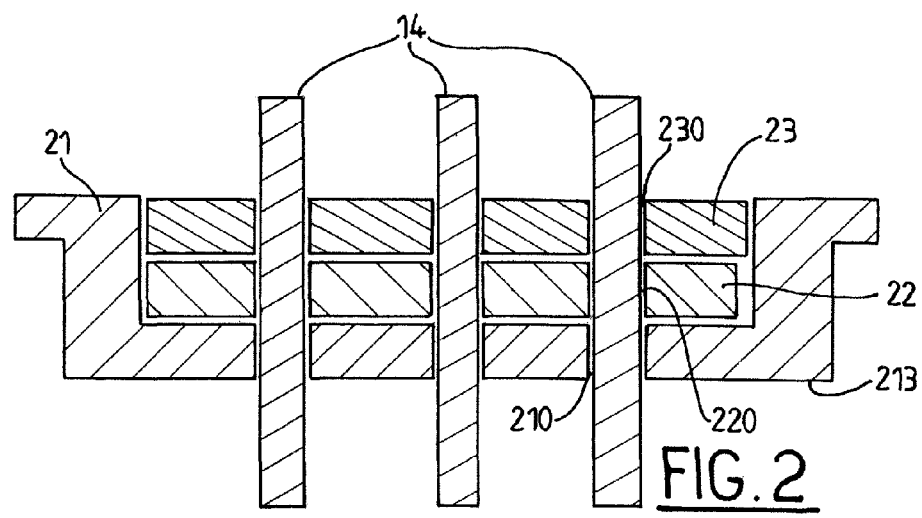
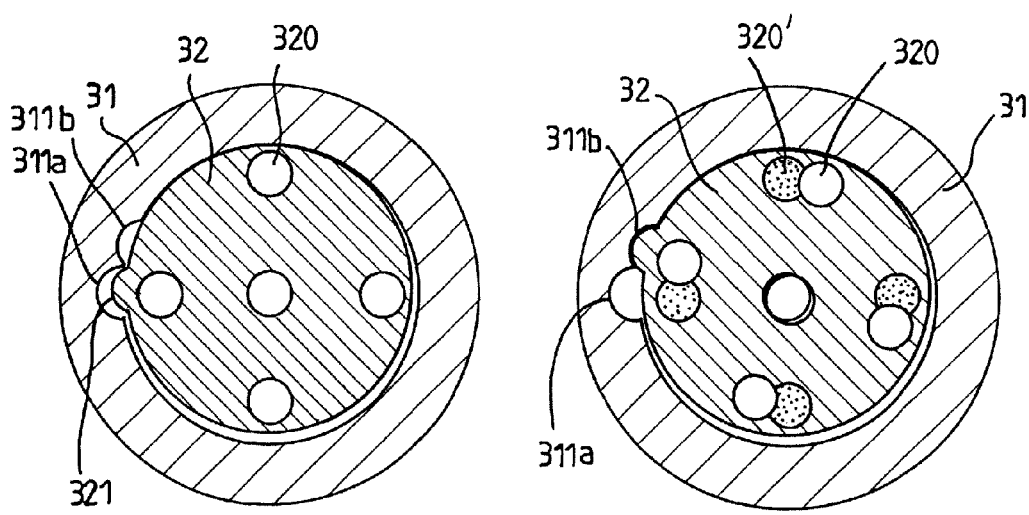

TRANSCRANIAL SECURING DEVICE FOR DEEP BRAIN STIMULATION LEADS

The present application claims the benefit to French Application No. 0805873, filed Oct. 23, 2008, which is herein incorporated by reference in its entirety.

FIELD OF THE INVENTION

The invention relates to a transcranial securing device for deep brain stimulation leads. The invention also relates to a deep brain stimulation system comprising such a securing device.

BACKGROUND OF THE INVENTION

Deep brain stimulation is a therapeutic technique involving implanting a medical appliance known as a cerebral stimulator that sends electrical impulses to specific portions of the brain. As an example, stimulation of the thalamic nucleus or the hypothalamus may be used to treat motor disorders such as tremor, caused in particular by Parkinson's disease, while stimulation of the subgenual cingulate cortex is in experimental use in the treatment of particularly severe forms of clinical depression that are resistant to treatment.

In all circumstances, a deep brain stimulation intervention comprises insertion into the cranium of the patient of a flexible lead guided by a cannula and/or a rigid stylus, until the tip of said lead reaches the region of the brain to be stimulated. Using a real time imaging procedure (especially nuclear magnetic resonance), coupled with electrophysiological exploration, means that the moment when the target region of the brain has been reached by the tip of the lead can be ascertained precisely. At this point, the insertion operation is halted, the stylus and/or the cannula are withdrawn from the lead, which is itself locked using a securing device that can ensure that it is held in place for a period that can attain several years.

The document "Medtronic—DBS™ Lead Kit for Deep Brain Stimulation 3387 3389—Implant Manual" from Medtronic Inc, which can be downloaded from the following website: http://www.medtronic.com/physician/activa/downloadablefiles/197928 b 006.pdf describes leads for deep electrical neurostimulation and a method of implanting them.

That document also describes a securing device comprising a part in the form of a sleeve for inserting into a cranial opening produced by craniotomy, and a cap that can be engaged with the sleeve to seal that opening. The sleeve-shaped part includes a collar that is intended to rest on the outer surface of the patient's cranium and that has radially oriented grooves. To secure an implanted lead using such a device, it is necessary to bend the proximal end (i.e. leaving the cranium) of said lead by about 90° and to introduce it into one of said grooves where it is kept in place by the cover.

Under such conditions, the operation of securing the lead has a tendency to cause small involuntary movements of its tip inside the patient's brain. Since the dimensions of the target regions that are to be stimulated are of the order of a few millimeters, such movements can considerably reduce the efficiency of stimulation.

Document U.S. Pat. No. 7,302,298 describes a deep brain stimulation lead kept in place by a screw thread that is introduced directly into an opening formed in the patient's cranium. That securing method suffers from the considerable drawback of causing rapid degradation of the passivation coating of the lead.

OBJECT AND SUMMARY OF THE INVENTION

The aim of the invention is to provide a securing device that can simply and reproducibly secure one or, as is preferable, several leads (for example in the range 1 to 10, typically 4 or 5) that critically need to be positioned relative to targets having millimeter-scale dimensions.

More particularly, the invention aims to provide a securing device that can rapidly lock a lead when its insertion is deemed to be satisfactory, while avoiding the introduction of involuntary and uncontrolled movements of its tip due to the locking operation.

In accordance with the invention, this aim may be achieved by a transcranial securing device for deep brain stimulation leads, comprising: a principal part in the form of a sleeve or cup for securing inside an opening formed in the cranium of a patient; and a first and a second securing part superimposed inside said principal part; said securing parts respectively comprising at least one axial bore adapted to allow the passage of one or more deep brain stimulation leads; wherein said securing parts are arranged so as to be capable of passing from a first relative position in which their respective axial bores are aligned to allow the lead or leads to slide axially, to a second relative position in which said axial bores are partially misaligned in order to grip the lead or leads, preventing said sliding.

In accordance with particular embodiments of the invention:

at least one of said first and second securing parts may be capable of passing from said first to said second position by rotation or rotation-translation about an axis parallel to said bores;

at least one of said first and second securing parts may be capable of passing from said first to said second position by translation in a direction perpendicular to said bores. More particularly, an eccentric turning part may be provided in order to move the first or the second securing part in translation in said direction perpendicular to the bores.

Advantageously, one of said securing parts may have at least one gripping element in the form of a tip or vee, which is capable of coming into contact with one of said leads, while the other securing part may have at least one support element disposed on an opposite side of the lead relative to the gripping element, such that when said first and second securing parts are in their second position, said or each lead is clamped between a corresponding gripping element and a support element;

the device may also comprise a means for locking said parts in their first relative position;

said securing parts may comprise a plurality of bores, each of which is adapted to allow the passage of one and only one deep brain stimulation lead.

In a further aspect, the invention provides a deep brain stimulation system comprising: a securing device as described above and at least one deep brain stimulation lead inserted in an axial bore of said device.

BRIEF DESCRIPTION OF THE DRAWINGS

Other characteristics, details and advantages of the invention become apparent from the following description made with reference to the accompanying drawings given by way of example and that are respectively as follows:

FIG. 1C shows a plan view of the second securing device of the device of FIGS. 1A and 1B;

FIG. 2 shows a sectional view of a device in accordance with one embodiment of the invention;

FIGS. 3A and 3B show two sectional views of a device in accordance with a first variation of said embodiment of the invention, in its first and second position respectively;

MORE DETAILED DESCRIPTION

The principle on which the various embodiments of the invention are based consists of gripping the lead or leads to be locked in an axial bore.

Figure 1A:
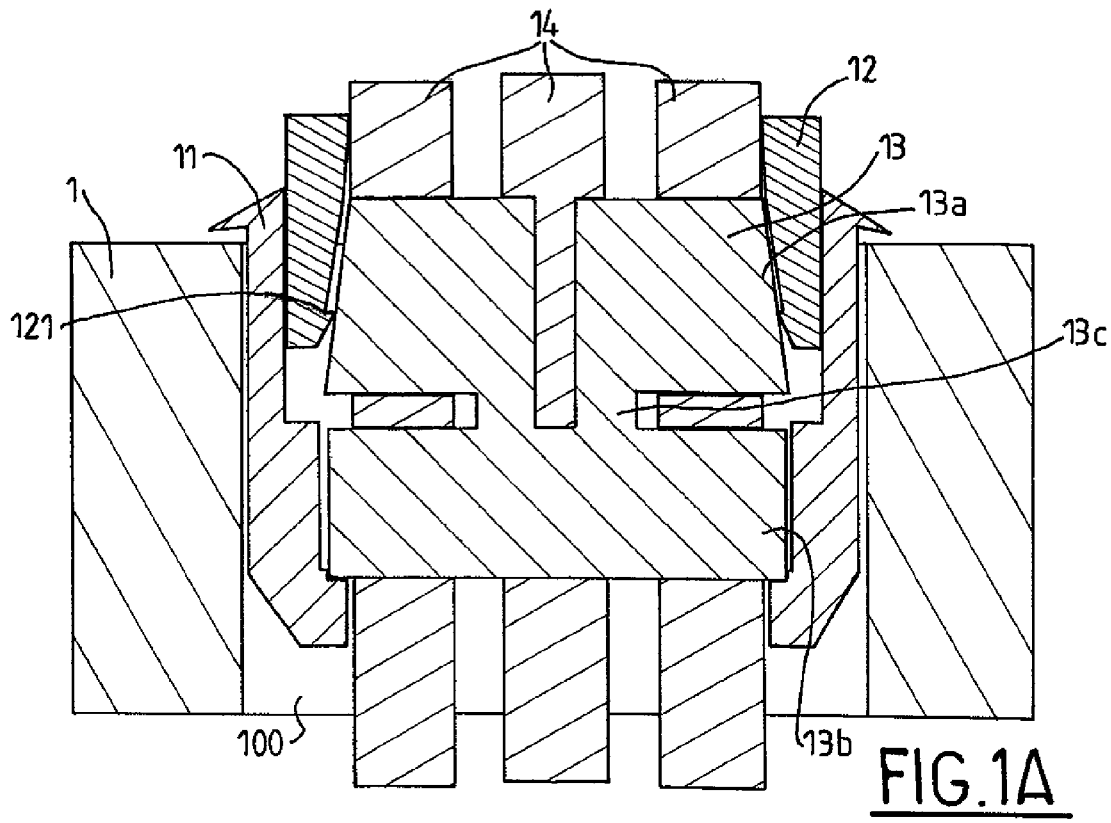
FIGS. 1A and 1B show two sectional views of a transcranial securing device for deep brain stimulation leads.
Figure 1B:
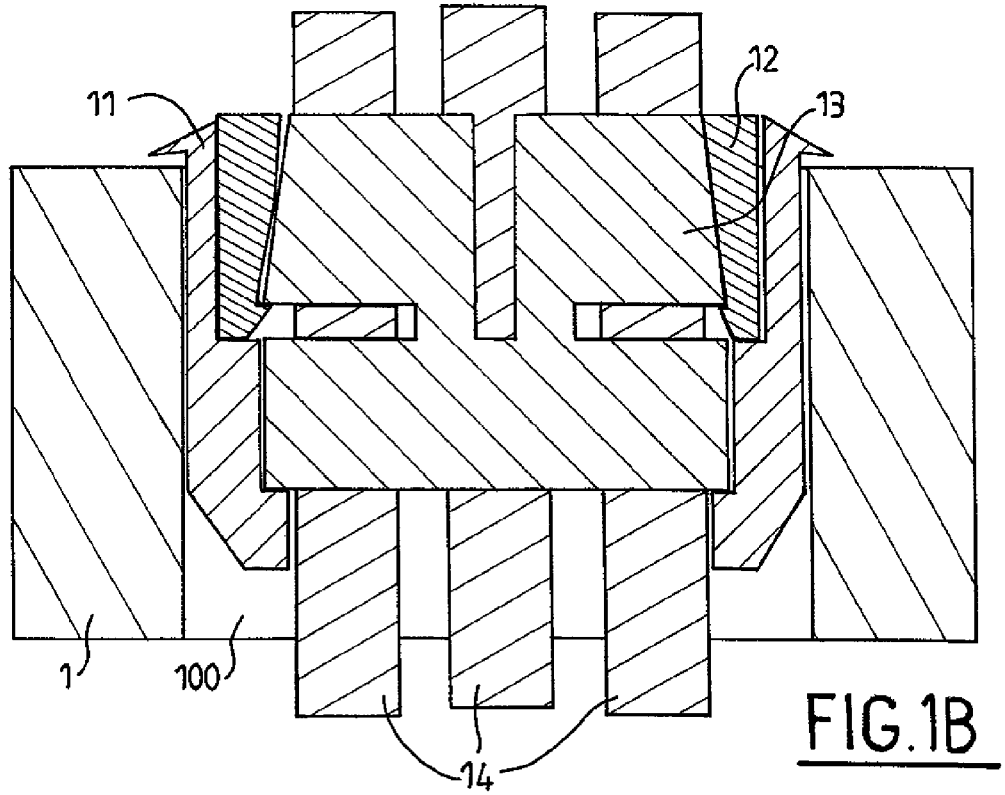

FIGS. 1A, 1B, and 1C illustrate a securing device comprising a part termed the principal part 11, in the form of a sleeve, which is intended to be introduced into an opening 100 formed by craniotomy in the cranium 1 of a patient; a first securing part 12 located at the side of the part in the form of a sleeve oriented towards the outside of the cranium 1; and a second securing part 13 located on the side of the part in the form of a sleeve oriented towards the inside of the cranium 1. The first and the second securing part have dimensions and shapes that allow them to be housed inside the principal part 11 in the form of a sleeve.

The first securing part 12 is also in the shape of a sleeve with a single axial bore having an inside surface that is tapered or pyramidal. The shape of the outer surface of this part matches that of the inner surface of the principal part 11.

The second securing part 13 has a plurality of axial bores 130 of axes that are parallel to the axis of the single bore of the principal part 11. Each of these bores is adapted to allow the passage of one and only one deep brain stimulation lead 14 (although in a variation it would be possible for each bore to pass several leads). FIG. 1C shows that in the example under consideration, the part 13 comprises five bores 130 disposed in the form of a cross.

More precisely, in the device of FIGS. 1A to 1C, the second securing part 13 is constituted by a first segment 13a and a second segment 13b connected together via elastic connections 13c. The first segment 13a, which is oriented towards the outside of the cranium 1, is divided into four parts or quarters by two cuts 131, 132 that pass through the bores 130.

The first segment 13a has a tapered or pyramidal outer surface that matches the shape of the inner surface of the first securing part to allow reciprocal push fitting of said two elements.

In order to implant a deep brain electrostimulation system using the securing system of FIGS. 1A to 1C, the following procedure is carried out.

Firstly, a hole 100 approximately 8 mm [millimeter] in diameter is formed in the cranium 1 of a patient by craniotomy, the axis of the hole being determined as a function of mapping the target or targets in the brain of that patient (for example the subthalamic nucleus for Parkinson's disease). The principal part 11 in the form of a sleeve is inserted into that hole, a collar being provided to act as an abutment upon insertion. The angular positioning of said principal part inside the hole can be ensured by a screw that is inserted in the collar in the manner of an angular abutment or a centering piece. Alternatively, the angular position of the part 11 may also be locked by bonding or pre-stressing.

Next, the target or targets are mapped more precisely by electrophysiological imaging using per-operative leads. The second securing part 13 is introduced into the sleeve 11, until it is positioned on a seat provided for this purpose; next, the first securing part 12 is positioned. At this stage, care is taken not to force fit the two securing parts.

One or, as is preferable, several stimulation leads (five in the example) are placed in an implantation robot for sliding into the bores 130 of the part 13.

When the insertion depth of the leads corresponds to the position of the targets mapped with the electrophysiological exploration leads, locking is carried out by causing the first part 12 to drop in order to push fit the two securing parts 12 and 13. Thus, the radial pressure exerted by the tapered inner wall of the first locking part 12 causes the various portions of the second securing part constituting the first segment 13a to come together. In this manner, the bores 130 of said second securing part tighten around the leads 14, which are thus firmly held.

Once insertion is complete, the ratchet 121 irreversibly locks the assembly. In a variation, this ratchet is not provided: in this manner, the assembly remains reversible simply by using frictional forces.

Parts 11, 12 and 13 are preferably cylindrically symmetrical in shape. They may thus be produced essentially by turning.

By way of example, the principal part 11 in the form of a sleeve may have an external diameter of 8 mm, an internal diameter of 6 mm and a height of 6 mm, with seats provided 5 mm (for the second securing part) and 3 mm (for the first securing part) from its edge located outside the cranium. Under such circumstances, the second securing part 13 may be constituted by a first tapered segment 13a with a height of 2.5 mm, a major base diameter of 6 mm and a minor base diameter of 5.4 mm; the second segment 13b may have a cylindrical shape with a height of 2 mm and a diameter of 6 mm; and the height of the elastic connecting elements 13b may be 0.5 mm. The diameter of the bores 130 prior to locking may typically be 1.45±0.1 mm. This diameter is slightly greater than that of the leads normally used in deep brain stimulation (1.27 mm for leads from Medtronic (registered trade mark)); before introducing the stimulation leads, it is in fact necessary to carry out an electrophysiological exploration of the targets, which is carried out using microleads that are introduced through cannulas with a diameter of approximately 1.45 mm. The holes on the securing parts must be compatible with said cannulas.

The materials employed must satisfy biocompatibility specifications for implantation lasting more than 28 days. As an example, medical grade PEEK (polyether-etherketone) or PTFE (polytetrafluoroethylene) may be used. Biocompatible metals exist, but are not preferred as they may generate artifacts on the nuclear magnetic resonance images; further, due to their rigidity, relatively large forces would be necessary to carry out the lead locking operation.

FIG. 2 shows a skeleton diagram of an embodiment of the invention which itself can be broken down into a plurality of variations. In this embodiment, a first securing part 22 and a second securing part 23, generally in the form of a plate or disk, are superimposed inside a principal part 21 in the form of a cup. The two securing parts have one or more respective axial bores 220, 230 that are aligned when said parts are in a relative first position and partially misaligned when said parts are in a second position. It should be understood that when the bores are aligned, the leads 14 can slide freely, whereas when they are misaligned, they are clamped between the securing parts and thus locked in position.

In the example of FIG. 2, the principal part 21 is defined as being "cup-shaped" as it has a bottom 213 oriented towards the inside of the cranium of a patient and is itself traversed by axial bores 210. In a variation, this part may be sleeve-shaped with an internal rim intended to keep the securing parts in place. However, the use of a principal cup-shaped part is preferred since the bores 210 contribute to holding the deep brain stimulation leads 14.

As with FIGS. 1A to 1C, the materials employed must satisfy biocompatibility specifications for implantation lasting more than 28 days. As an example, medical grade PEEK (polyether-etherketone) or PTFE (polytetrafluoroethylene) may be used.

FIGS. 3A and 3B illustrate a first variation of a device in accordance with this embodiment of the invention.

In these figures, reference numerals 31 and 32 indicate the principal part and the first securing part respectively; the second securing part is not visible as it is located below the part 32.

The two securing parts are in the shape of a disk and each comprises five axial bores 320 of diameter that is adapted to allow a stimulation lead to pass through. The second part is integral with the principal part; in the limit, these two parts could be produced as a single piece. In contrast, the first securing part 32 may be moved inside the principal part by a rotation-translation movement—the amplitude of the rotation typically being 5° to 20°—in order to misalign its bores 320 relative to those (not shown) of the second securing part. If there is no bore in the central position, a purely rotational movement would be sufficient.

It should be noted that the central lead, when present, is necessarily gripped less firmly than the others. As a consequence, this variation is more suitable for a configuration with four bores and four leads.

FIG. 3A shows the securing device when the bores of the various parts are aligned; in FIG. 3B, reference numerals 320 indicate the bores in the misaligned position, while the reference numerals 320' indicate, for comparison, these same bores in the aligned position.

A radial projection or peg 321 provided on the outer surface of the part 32 and two notches 311a, 311b with different dimensions (in the examples shown in the figures, notch 311b is substantially smaller than notch 311a) on the inner surface of the principal part 31 allow the second securing part to be reversibly locked in its two extreme positions.

Under these conditions, a rotational movement of 32 relative to 31 bringing the peg 321 from the "large" notch 311a to the "small" notch 311b causes translation of the part 32 in a plane perpendicular to the axis of the bores 320. Such a translation has an amplitude of a few hundred µm [micrometer], typically approximately 350 µm. Its effect is to constrain the securing part 32 and clamp the leads inside the bores.

In accordance with a second variation of the embodiment of the invention, illustrated in FIGS. 4A to 4D, the misalignment of the axial bores which blocks the stimulation leads in place is produced by a relative translational movement of the two securing parts. This is the variation that apparently offers the best performance.

The device of FIGS. 4A to 4D comprises a principal part 41 in the form of a cup provided with a bottom 413 as well as a first and a second superimposed securing part (reference numerals 42 and 43). These three elements have axial bores 410, 420 and 430 which, in a first position, are aligned in order to allow the stimulation leads 14 to slide and in a second position they are misaligned in order to lock said leads. More precisely, the offset is produced by a movement of the first securing part in a direction perpendicular to the axis of the bores. This movement may be caused by rotation of an eccentric part or peg 45. Advantageously, the upper portion of said peg may be produced in a manner that enables it to readily receive a tool intended to cause it to turn; as an example, it may comprise a groove intended to receive the blade of a screwdriver.

Figure 4A:
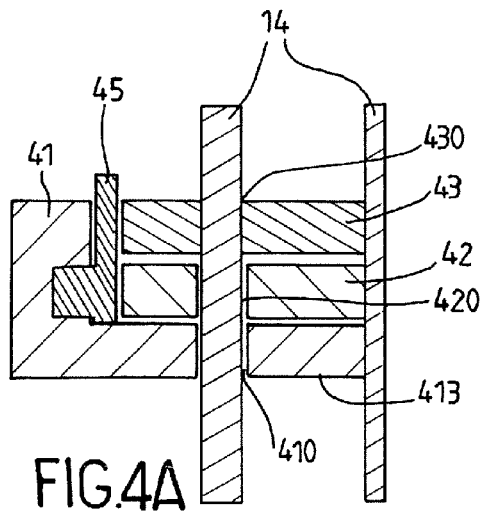
FIGS. 4A and 4B show two sectional views of a device in accordance with a second variation of said embodiment of the invention in its first and second position respectively.
Figure 4B:
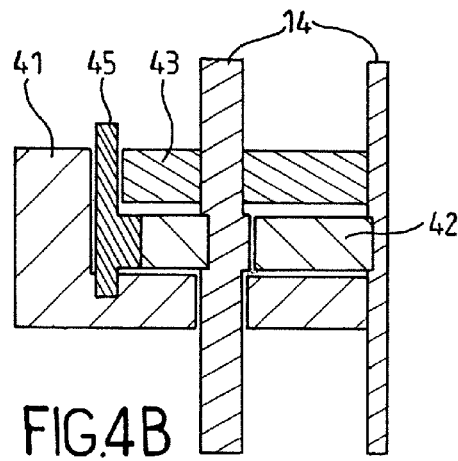
Figure 4C:
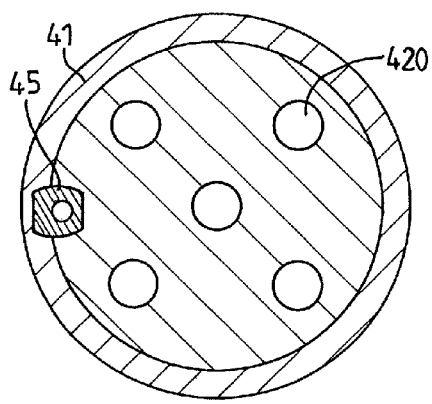
FIGS. 4C and 4D show plan views corresponding to FIGS. 4A and 4B respectively.
Figure 4D:
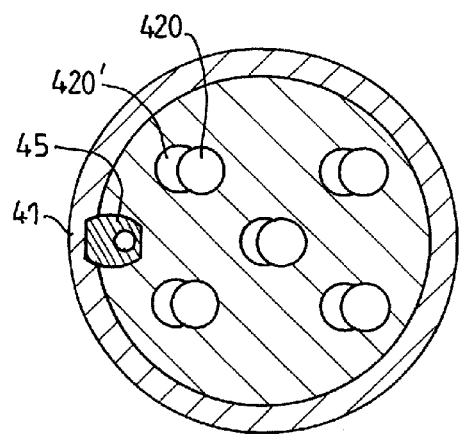

FIGS. 4A and 4B show a partial sectional view of the device in its first and second positions respectively. FIGS. 4C and 4D show a plan view of this device, also in its first and its second position, the second securing part having been removed to allow the first part 42 to be seen. It should be noted that the first securing part has a flat on which the peg 45 acts; its diameter is less than that of the principal part 41 in order to provide the clearance necessary for the translational movement. The geometry of this part is such that the "gripped leads" or "free leads" positions correspond to two positions of mechanical equilibrium. Because twisting forces are applied to the part 45, it is preferably produced from biocompatible metal (medical grade stainless steel or titanium).

Figure 4E:
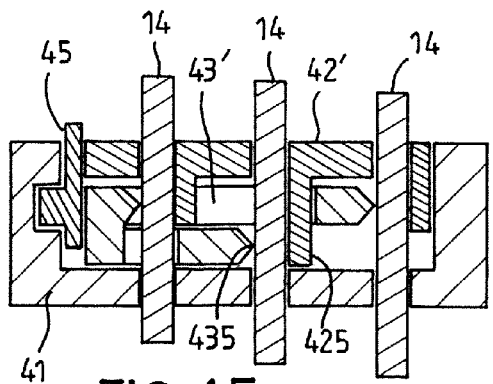
FIGS. 4E and 4F show two sectional views of a device in accordance with a third variation of said embodiment, which is particularly suitable for gripping small diameter leads, in its first and second position respectively.
Figure 4F:
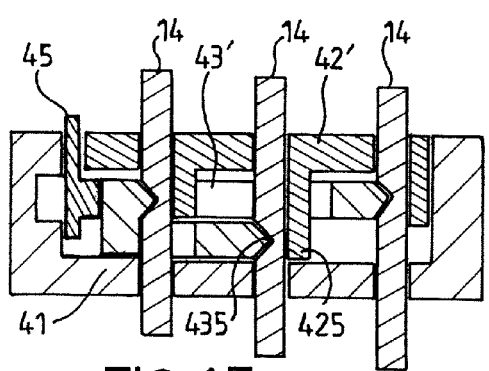

The device of FIGS. 4A to 4D is particularly suitable for gripping leads with a diameter of more than 1 mm, typically in the range 1 mm to 1.5 mm. With leads of smaller dimensions (diameter in the range approximately 300 µm to 1 mm), it is preferable to use the variation shown in FIGS. 4E (free position) and 4F (gripped position). In such a device, the second gripping part 43' comprises gripping elements 435 in the form of a tip or vee, and the first part 42' of support elements in the form of a partition 425 extend in a vertical direction (i.e. parallel to the direction of sliding or the leads). The gripping elements 435 are arranged to compress the leads 14 against the corresponding support elements which function as anvils. Thus, the leads are fixed by localized clamping. It is also possible to envisage a complementary arrangement in which the gripping elements are carried by the first securing part and the support elements by the second part.

It should be noted that the gripping elements 435 for the various leads may be located in different planes.

All of the devices shown in the figures and described in detail above are adapted for securing five leads, but this in no way constitutes a limitation to the invention. The number of leads may be in the range 1 to 10, or even more. The use of four or five leads appears to be particularly preferable.

What is claimed is:

1. A transcranial securing device for deep brain stimulation leads, comprising:
    a principal part in the form of a sleeve or cup for securing inside an opening formed in the cranium of a patient; and
    a first and a second securing parts superimposed inside said principal part for securing one or more deep brain stimulation leads;
    said securing parts respectively comprising at least one axial bore adapted to allow the passage of one or more deep brain stimulation leads;
    wherein said securing parts are arranged so as to be capable of passing from a first relative position in which their respective axial bores are aligned to allow the lead or leads to slide axially, to a second relative position in which said axial bores are partially misaligned in order to grip the lead or leads, preventing said sliding.

2. A device according to claim 1, wherein at least one of said first and second securing parts is capable of passing from said first to said second position by rotation or rotation-translation about an axis parallel to said bores.

3. A device according to claim 1, wherein at least one of said first and second securing parts is capable of passing from said first to said second position by translation in a direction perpendicular to said bores.

4. A device according to claim 3, wherein an eccentric turning part is provided in order to move the first or the second securing part in translation in said direction perpendicular to the bores.

5. A device according to claim 3, wherein one of said securing parts has at least one gripping element in the form of a tip or vee, which is capable of coming into contact with one of said leads, while the other securing part has at least one support element disposed on an opposite side of the lead relative to the gripping element, such that when said first and second securing parts are in their second position, said or each lead is clamped between a corresponding gripping element and a support element.

6. A device according to claim 1, also comprising a means for locking said securing parts in their first and second relative positions.

7. A device according to claim 1, wherein said securing parts comprise a plurality of axial bores, each of which is adapted to allow the passage of one and only one deep brain stimulation lead.

8. A deep brain stimulation system comprising:
   a securing device according to claim 1; and
   at least one deep brain stimulation lead inserted into an axial bore of said device.

* * * * *